US00PP21550P3

(12) United States Plant Patent
Bernabe

(10) Patent No.: US PP21,550 P3
(45) Date of Patent: Nov. 30, 2010

(54) *SALVIA* PLANT NAMED 'PLUENN'

(50) Latin Name: *Salvia jamensis*
Varietal Denomination: Pluenn

(76) Inventor: Catherine Bernabe, Saint Gueltas, Henansal (FR) 22400

( * ) Notice: Subject to any disclaimer, the term of this patent is extended or adjusted under 35 U.S.C. 154(b) by 0 days.

(21) Appl. No.: 12/459,813

(22) Filed: Jul. 7, 2009

(65) Prior Publication Data

US 2009/0328267 P1 Dec. 31, 2009

(51) Int. Cl.
*A01H 5/00* (2006.01)

(52) U.S. Cl. ..... Plt./475

(58) Field of Classification Search ..... Plt./263, Plt./475

See application file for complete search history.

(56) References Cited

PUBLICATIONS

UPOV-ROM GTITM, Plant Variety Database, 2010/02, GTI Jouve Retrieval Software, citation for 'Pluenn'.*

* cited by examiner

*Primary Examiner*—Susan B McCormick Ewoldt

(57) ABSTRACT

A new and distinct *Salvia* cultivar named 'PLUENN' is disclosed, characterized by Bright pink flowers, large individual flower size and early flowering. 'PLUENN' is highly floriferous and has a compact, upright plant habit. The new variety is a *Salvia,* normally produced as an outdoor garden or container plant.

1 Drawing Sheet

Figure 1:
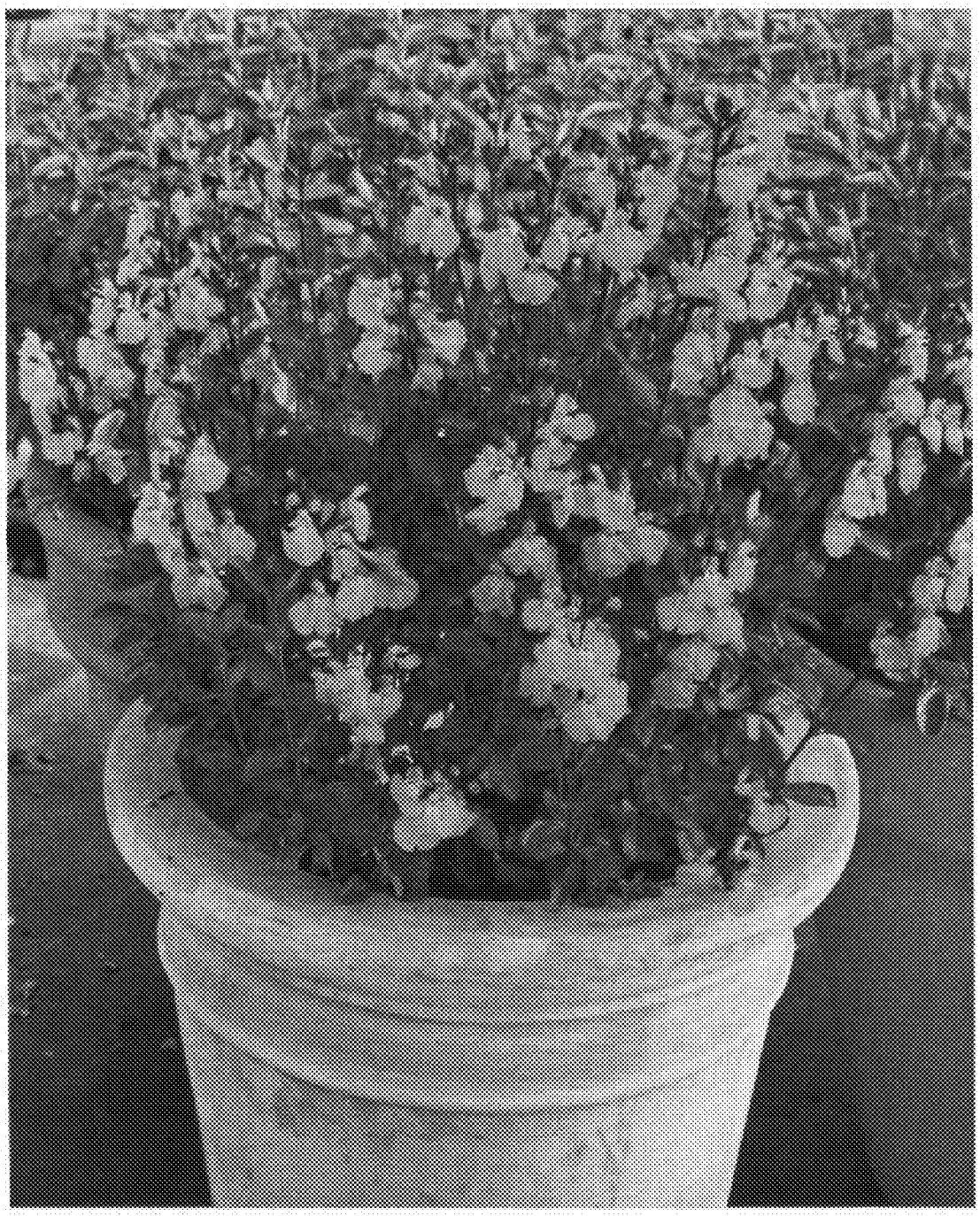

Latin name of the genus and species: *Salvia jamensis.*
Variety denomination: 'PLUENN'.

BACKGROUND OF THE INVENTION

The new cultivar is a product of a planned breeding program conducted by the inventor, Catherine Bernabe, a citizen of France. The objective of the breeding program was to produce highly floriferous plants of *Salvia jamensis* in a variety of colors. Plants of the unpatented variety *Salvia jamensis* were self-crossed during the Summer of 2002, at a commercial nursery in Henansal, France. The new variety was discovered in the Summer of 204, at the same commercial nursery by the inventor, Catherine Bernabe, in a group of seedlings resulting from that crossing.

Asexual reproduction of the new cultivar 'PLUENN' by vegetative cuttings was performed at the same commercial greenhouse in Henansal, France in 2005 and has shown that the unique features of this cultivar are stable and reproduced true to type on successive generations. All plants of 'PLUENN' have been kept confidentially at the nursery in Henansal, France, with the exception of those supplied for Plant Breeders' Rights testing in Spring of 2009. Plant Breeders' Rights were applied for in April of 2008, however, there has been no commercial distribution or access to the variety.

SUMMARY OF THE INVENTION

The cultivar 'PLUENN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PLUENN' These characteristics in combination distinguish 'PLUENN' as a new and distinct *Salvia* cultivar:

1. Bright pink flowers.
2. Large individual flower size.
3. Compact and upright plant habit.
4. Early flowering.
5. Highly floriferous.

Plants of the new cultivar 'PLUENN' are similar to plants of the parent, *Salvia jamensis* unpatented, in most horticultural characteristics, however, plants of the new cultivar 'PLUENN' produce larger flowers than the parent variety, with longer inflorescence.

COMMERCIAL COMPARISON

Plants of the new cultivar 'PLUENN' can also be compared to *Salvia microphylla.* Plants of 'PLUENN' are similar to plants of, *Salvia microphylla,* unpatented, in most horticultural characteristics, however, plants of the new cultivar 'PLUENN' produce larger flowers, with longer inflorescence. 'PLUENN' also flowers earlier than *Salvia microphylla,* and produces overall more flowers and more inflorescence than *Salvia microphylla.*

Plants of the new cultivar 'PLUENN' can also be compared *Salvia jamensis* 'La Siesta' unpatented. Plants of 'PLUENN' are similar to plants of, *Salvia jamensis* 'La Siesta' most horticultural characteristics, however, plants of the new cultivar 'PLUENN' flower earlier, produce more flowers of a brighter color than 'La Siesta.' 'PLUENN' also produces a more compact overall plant.

BRIEF DESCRIPTION OF THE PHOTOGRAPH

The accompanying photograph in FIG. 1 illustrates in full color a typical plant of 'PLUENN' in an approximately 2 liter pot. Age of the plant photographed is approximately 30 weeks from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'PLUENN' plants grown in an unheated plastic covered greenhouse at a commercial nursery in Henansal, France. The growing temperature ranged from 8° C. to 28° C., day and night. The nursery area is un-shaded, giving bright, normal sunlight conditions. Measurements and numerical values represent averages of typical plant types.

Botanical classification: *Salvia jamensis* 'PLUENN'.

PROPAGATION

Time to initiate roots: About 10 days at approximately 20° C.

Time to produce a rooted cutting: About 20 to 25 days at 20° C.

PLANT

Plant spread: Approximately 45 to 50 cm.

Length of primary lateral branches: Approximately 20 to 25 cm from stem to just under the inflorescence.

Diameter of lateral branches: Approximately 0.3 cm.

Quantity of lateral branches: About 50 to 60 per plant.

Stem:

- *Color.*—Youngest near RHS Yellow-Green 145A. Oldest near RHS Yellow Green 147A.
- *Texture/pubescence.*—Smooth, non-pubescent.

Internode length: Approximately 5.5 to 7 cm.

Age of plant described: Approximately 30 weeks from a rooted cutting in early spring.

Pot size of plant described: 2 liter.

FOLIAGE

Leaf:

- *Arrangement.*—Opposite.
- *Quantity.*—Approximately 10 per main branch.
- *Average length.*—Approximately 4.5 cm.
- *Average width.*—Approximately 1.7 cm.
- *Shape of blade.*—Elliptic to oblong.
- *Apex.*—Obtuse.
- *Base.*—Attenuate.
- *Attachment.*—Stalked.
- *Margin.*—Crenate.
- *Texture of top surface.*—Glossy.
- *Pubescence.*—Slightly on top face, non-pubescent on underside.
- *Color.*—Young foliage upper side: Near RHS Yellow-Green 144A. Young foliage under side: Near RHS Yellow-Green 144A. Mature foliage upper side: Near RHS Yellow-Green 147A. Mature foliage under side: Near RHS Yellow-Green 146A.
- *Venation.*—Type: Pinnate. Venation color upper side: Near RHS Yellow-Green 144C. Venation color under side: Near RHS Yellow-Green 144C.
- *Petiole.*—Average Length: Approximately 1 cm. Diameter: Approximately 0.1 cm. Color: Near RHS Yellow-Green 144C.

FLOWER

Natural flowering season: May to November.

Inflorescence type and habit: Flowers arranged in verticillasters on spikes.

Flower longevity on plant: 8 days.

Quantity of flowers: About 8 to 10 buds and 6 to 8 fully opened flowers per lateral branch, at one time; or about 50 to 60 blooming spikes per plant.

Inflorescence size:

- *Diameter/width.*—Approximately 5 cm.
- *Height.*—Approximately 15 to 17 cm.

Peduncle:

- *Length.*—0.7 cm.
- *Diameter.*—0.1 cm.
- *Color.*—Near RHS Greyed-Purple N187B.
- *Orientation.*—Completely straight and upright, no angle or curve.
- *Strength.*—Rigid.

Petals:

- *Petal arrangement.*—Bilabiate flowers arranged in verticillasters on spikes.
- *Margin.*—Entire.
- *Length.*—Lower lip: Approximately 0.3 cm upper lip: Approximately 2.5 cm.
- *Width.*—Lower lip: Approximately 0.2 cm upper lip: Approximately 0.5 cm.
- *Petal quantity.*—5, with 2 fused on lower lip, 3 fused on upper lip.
- *Apex.*—Obtuse.
- *Texture.*—Glossy.

Color:

- *Petals.*—When opening: Upper surface: Near RHS Red 53C with Yellow 10C. Lower surface: Near RHS Red 53C with Yellow 10C.
- *Fully opened.*—Upper surface: Near RHS Red 47D. Lower surface: Near RHS Red 48B.

Bud:

- *Shape.*—Elongated cylinder.
- *Length.*—Approximately 1 cm.
- *Diameter.*—Approximately 0.5 cm.
- *Color.*—Near RHS Violet 83A.

Sepals:

- *Shape.*—Quantity per flower: 3.
- *Length.*—Approximately 1.5 cm.
- *Width.*—Approximately 0.7 cm, fused at base.
- *Margin.*—Entire.
- *Texture.*—Slightly pubescent.
- *Color.*—Near RHS Brown 200B and Yellow-Green 144B.

REPRODUCTIVE ORGANS

Stamens:

- *Number.*—2.
- *Filament length.*—Approximately 1.5 cm.

Anthers:

- *Shape.*—Linear.
- *Length.*—Approximately 0.2 cm.
- *Color.*—Near RHS Greyed-Green 198C.
- *Pollen.*—Color: Near RHS Yellow-Orange 14B. Quantity: Scant.

Pistil:

*Number.*—1.

*Length.*—Approximately 2.7 cm.

*Style.*—Length: Approximately 2.4 cm. Color: Near RHS White 155D.

*Stigma.*—Color: Near RHS red purple N 74B. Ovary color: Near RHS Yellow 9C.

OTHER CHARACTERISTICS

Seeds and fruits: 4 spherical seeds per flower, each less than 0.1 cm in diameter.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'PLUENN' as herein illustrated and described.

* * * * *